(12) United States Patent
Ross

(10) Patent No.: US 6,869,412 B2
(45) Date of Patent: Mar. 22, 2005

(54) METHOD AND DEVICE FOR INTRAVASCULAR PLASMA FLUID REMOVAL

(76) Inventor: Edward Allan Ross, 8917 SW. 42nd Pl., Gainesville, FL (US) 32608

( * ) Notice: Subject to any disclaimer, the term of this patent is extended or adjusted under 35 U.S.C. 154(b) by 335 days.

(21) Appl. No.: 10/054,483

(22) Filed: Nov. 13, 2001

(65) Prior Publication Data
US 2002/0115956 A1 Aug. 22, 2002

Related U.S. Application Data

(60) Provisional application No. 60/247,238, filed on Nov. 13, 2000.

(51) Int. Cl.⁷ .......................... A61M 37/00; C02F 1/44
(52) U.S. Cl. ...................... 604/6.09; 604/8; 604/6.04; 210/645
(58) Field of Search .............. 604/4.01, 5.01, 604/6.01, 6.04, 5.03, 6.09, 6.11, 6.16, 7–9; 210/645, 739, 741, 416.1, 500.21, 500.23

(56) References Cited

U.S. PATENT DOCUMENTS

| | | | |
|---|---|---|---|
| 4,235,231 A | * | 11/1980 | Schindler et al. ......... 604/6.09 |
| 5,151,082 A | * | 9/1992 | Gorsuch et al. ........... 604/5.04 |
| 5,324,518 A | * | 6/1994 | Orth et al. ................ 424/423 |
| 5,980,478 A | * | 11/1999 | Gorsuch et al. ........... 604/5.04 |

\* cited by examiner

*Primary Examiner*—Angela D. Sykes
*Assistant Examiner*—Leslie R. Deak
(74) *Attorney, Agent, or Firm*—Sheldon Palmer

(57) ABSTRACT

Plasma fluid removal is needed in a variety of clinical conditions including congestive heart failure and moderate renal insufficiency. In order to avoid the problems inherent in extracorporeal ultrafiltration methods, the present invention removes fluid using an intravascular or intracorporeal dual-lumen catheter. Plasma fluid is driven across a semi-permeable membrane, as in an in vivo vascular catheter. Suboptimal intracatheter flow, luminal collapse, erratic high transmembrane flow with nonhomogenous caking and clotting of the external catheter surface are all avoided by inducing pressure gradients across the wall by means of osmotic forces instead of negative pressures induced by hydraulic pumps. Osmotically induced fluid flow would tend to keep the lumena slightly distended and thereby simplify the fluid delivery systems. Osmotic gradients are maintained by utilizing dual lumen catheters typically placed in large central veins, and attached to pumps supplying high osmolality sterile solutions (such as dextrose or other sugars). Such a sealed system using readily available sterile sugar solutions and biocompatible catheter substrate would be extremely safe.

28 Claims, 2 Drawing Sheets

METHOD AND DEVICE FOR INTRAVASCULAR PLASMA FLUID REMOVAL

CROSS-REFERENCE TO RELATED APPLICATIONS

This is a non-provisional application based on and claiming the benefit of the filing date of provisional application Ser. No. 60/247,238; filed Nov. 13, 2000.

STATEMENT REGARDING FEDERALLY SPONSORED RESEARCH OR DEVELOPMENT

"Not Applicable"

REFERENCE TO A MICROFICHE APPENDIX

"Not Applicable"

BACKGROUND OF THE INVENTION

1. Field of the Invention

This invention relates to methods for the removal of plasma fluid from a patient in need thereof, including those in what may be called a disease state, for example, congestive heart failure or moderate renal insufficiency, both of which are typically characterized by fluid overload. The invention also relates to intravascular devices for effecting the plasma fluid removal.

2. Description of the Related Art including information disclosed under 37 CFR 1.97 and 1.98.

There are a number of techniques described in the art for removing plasma fluid from a patient. Many patients treated using some of the more conservative of these techniques, such as high dose diuretics or cardiac inotropes fail to adequately respond. In such cases, the use of more invasive, risky, expensive, and/or labor-intensive therapies, such as intermittent hemodialysis or continuous veno-venous hemodialysis or hemofiltration are indicated. While these extracorporeal techniques are traditionally utilized to treat kidney failure, in the presence of fluid overload they can instead result in the removal of bulk fluids by the use of hydraulically, or pump-driven ultrafiltration across a dialyzer (i.e. "an artificial kidney"). It is the extracorporeal processing of blood in these prior art techniques that makes them less than optimal for the desired purposes.

The U.S. patent literature includes a number of prior patents, which, for the sake of easy understanding have been divided into four categories. The first category is one dealing with so-called "probes." These patents; U.S. Pat. Nos. 5,706,806, 5,607,390, 5,735,832 and 5,106,365, generally disclose devices having sealed ends and which allow fluid to flow to the end of the probe and then back. These devices are made for insertion into body tissues or fluids and are used for diagnostic, not treatment purposes. When using these devices, the analyte of interest diffuses into the probe and then out to an instrument, typically, a measuring instrument. These devices allow monitoring of a patient's pH, oxygen, sodium, potassium, etc. levels in the tissue of interest (blood, muscle, gut, brain, etc).

The second category includes so-called intravascular devices for plasmapheresis. There are a number of these patents by Gorsuch and Co-workers. These patents disclose the diffusion of plasma across semi-rigid membranes in highly complex shapes, but do so in order to remove deleterious plasma proteins. They do not specifically address the removal of fluid/water, even though a "byproduct" of the described techniques is removal of the fluid in which the deleterious proteins reside. In fact, in traditional plasmapheresis, there is no desire or intent to remove fluid per se, so that usually, the water volume is intentionally restored by re-infusing sterile fluids. In addition, some complex devices have been designed to remove targeted proteins from the extracorporeal plasma, and then return the rest of the plasma to the patient (as disclosed in Gorsuch U.S. Pat. No. 4,950,224 and 5,224,926). Additionally, Gorsuch U.S. Pat. No. 5,735,809 states " . . . the separated plasma may be treated for removing antibodies, antigens, pathogens, toxins and other undesirable materials." In Gorsuch, there is no teaching of merely removing fluid in the treatment of volume-overload states. Gorsuch, in U.S. Pat. No. 5,980,478, specifically indicates a desire to be able to remove the plasma fluid in its entirety and replace fluids separately as deemed necessary. This is in essence, a "poor man's dialysis," and much is made of the fact that it would preclude the need for purchasing dialysis equipment. Gorsuch refers to this technique as "PUT," as in Plasma Ultrafiltration Therapy. This device still removes plasma with all its constituent proteins. (both good and bad), because Gorsuch specifically makes note of a sieving coefficient cutoff of between $2\times10^4$ and $4\times10^6$ Daltons. The reason for this is that this method utilizes the older Gorsuch plasmapheresis technology. This presents a problem because the method is not safe for patients since the high volumes of ultrafiltrate will contain many important and beneficial proteins, and the patient may be seriously jeopardized if the fluid is continuously discarded.

The third category includes patents directed to intravascular hemodialysis devices, such as U.S. Pat. Nos. 4,235,231; 5,968,004; and 5,980,478. U.S. Pat. No. 5,902,336 is directed not to an intravascular device, but rather to a device surgically connected to a blood vessel and drains directly into the patient's own bladder for fluid removal.

The fourth category includes U.S. Pat. No. 4,563,170; 5,360,397; 6,030,358; 6,238,366; and 6,234,991. The '170 and '397 patents are not relevant since they are extracorporeal in nature and are variations on traditional blood purification devices such as hemodialysis. The '358 patent is not relevant since it discloses a microcatheter to deliver a therapeutic agent into a tissue. The '366 patent is not relevant since it is an extracorporeal fluid management device to help nursing staff keep track of input/output so as to balance fluid administration. Finally, the '991 patent is not relevant because it describes a method of enhancing peritoneal dialysis clearances.

BRIEF SUMMARY OF THE INVENTION

The invention provides, in one aspect thereof, an intravascular device for removing plasma from a patient's whole blood. The device is a sealed dual lumen catheter, i.e., a catheter comprising at least two channels, preferably in coaxial configuration, and allowing fluid entry into one channel and fluid egress, or exit via a direct connection to the other channel. The device is placed within a patient's blood vessel, and plasma from the patient's blood is driven through the catheter wall into the device by osmotic forces created by a hyperosmotic fluid which is continuously supplied through said lumens. The device is so constructed as to enable whole blood to come into contact with a semipermeable, hydrophilic membrane such as preferably, a hydrophilic polyamide, a modified polytetrafluoroethylene, i.e., one similar to Teflon® or a polyether sulfone forming the outer surface of the body of the catheter, whereby the plasma fluid portion thereof passes through the membrane due to the osmotic pressure exerted by a hyperosmotic fluid, preferably dextrose, but also including larger sugars such as disaccharides, oligosaccharides, starches, and low molecular weight dextrans flowing along its inner surface within a lumen of said device. Fresh hyperosmotic fluid is continuously supplied by the second lumen of the dual lumen device. Thus, the plasma fluid is removed from whole blood, in vivo. The invention also provides a method of removing plasma fluid from whole blood by utilizing the device, which is inserted into a patient's blood vessel.

The invention also overcomes some of the shortcomings of known extracorporeal methods by separating plasma fluid from the particulate blood components (i.e. red blood cells, white blood cells, platelets) intracorporeally, by using the device within a blood vessel. Thus osmotic pressure is utilized instead of the negative hydraulic pressure induced by pumped methods as described in the prior art.

DETAILED DESCRIPTION OF THE INVENTION

Figure 1:
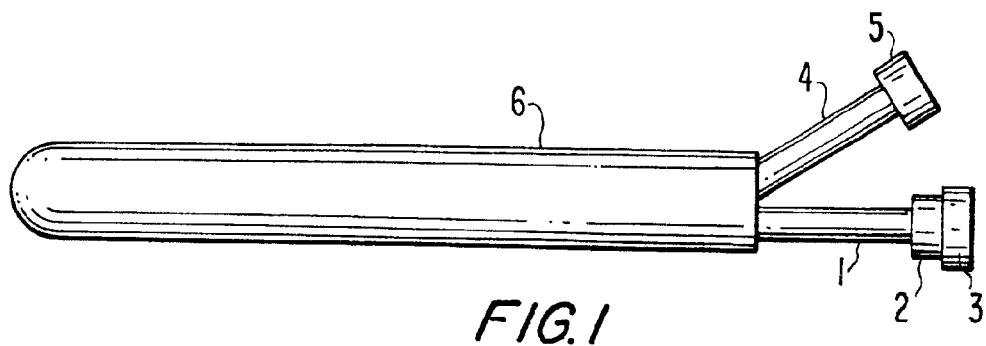
FIG. 1 is an external plan view of the device.

The primary therapeutic goal of the method of the invention performed using the device is removal of fluid volume, rather than the small amounts of solutes or toxins that are cleared by the convection of bulk liquid. The osmotic gradient or pressure required to induce the necessary rate of fluid removal will depend on the permeability of the device's wall (i.e. ultrafiltration coefficient) and its surface area. Increasing the porosity of the semipermeable barrier not only increases fluid loss, but also reduces its effective sieving and thereby allows convective losses of larger solutes or toxins. Intra-device collapse and flow irregularities are avoided in the present invention by using osmotic gradients, which distend the internal lumens. This is an important conceptual difference between the effects of prior art pump-driven hydraulic pressure gradients and osmotic gradients. Although the ultrafiltration coefficient of the semipermeable membrane suggests that there would be equal fluid losses for comparable pressure gradients, the device would not perform as well nor be as long-lived if it were vacuum-driven.

The semipermeable membrane used in the invention is formed, preferably of a highly biocompatible and hydrophilic material, having a high ultrafiltration coefficient and a molecular weight cut-off below that of the osmotic agent, i.e., 180 Daltons in the case of dextrose. There are a number of permutations and variations in the types of membranes that may be devised to achieve the desired goal. In a preferred embodiment, the membrane is a polymeric flexible membrane. Among these are a) hydrophilic polyamides; b) hydrophobic fluorocarbons, such as the hydrophobic polytetrafluoroethylene (PTFE) [Dupont's Teflon®] modified to make them more hydrophilic (such as with charged molecules as in Dupont's Nafion®; c) polyether sulfone; d) siloxanes or polysiloxanes; or e) polysulfones. Another approach to the problem is to impose size selectivity of the membrane with a thin layer of a tight polymeric membrane, (such as a polysulfone) and to maintain the structural integrity of the membrane with a separate and highly porous skeleton layer (such as a polysulfone or a polyurethane). Such dual layered membranes are typically made by a process of co-extrusion of the polymers; or a process in which one of the polymers is sprayed as a layer on top of the underlying polymer, which is the support structure.

The feasibility of applying the concept for human use is demonstrated by calculating predicted osmotic losses. Typical patient applications medically necessitate removing 2–3 ml of plasma fluid/minute, for a total of up to about 3–4 liters/day. Polymer or silicone-based membranes can be formed by extruding them in the shape of catheters or flat sheets that are turned into tubes by means of a seam, and can easily have ultrafiltration coefficients ranging from single digit amounts to as much as 50 ml/hour/m$^2$ membrane/mm Hg transmembrane pressure. As a practical example, one can utilize a membrane with an ultrafiltration coefficient of 10 ml/hour/m$^2$/mm Hg gradient in order to remove 3 ml/min (180 ml/hour). An intravenous catheter, such as those placed in the inferior vena cava by way of the femoral vein, can have surface areas in the range of 20 cm$^2$. One can then calculate the necessary pressure gradient to produce this goal of 180 ml/hour using a 0.002 m$^2$ device with a coefficient of 10 ml/hour/m$^2$/mm Hg pressure. This yields a value of 9000 mm Hg. One can convert that pressure gradient from mm Hg to the equivalent milliosmole gradient by dividing by the 19.33 conversion factor, yielding 466 milliosmoles/kg water. Since human whole blood has an osmolality of approximately 300 milliosmoles/kg and since non-ideal conditions are often considered to have only about 93% efficiency, the device's lumen would need to have an osmolality of approximately 824 milliosmoles/kg. That osmolality could easily be provided by fluids currently commercially available and typically in use for other applications in a hospital setting, such as sterile 20% dextrose solutions. The gradient is maintained by optimizing the flow rate for supplying fresh solution.

As pointed out above, fluid removal is most effective when it is osmotically driven across the device's external surface comprising a semipermeable membrane or barrier, and into a lumen of the catheter. In a simple embodiment of this concept, the device is a dual lumen catheter of coaxial configuration, and the two lumina (the inner and the outer lumina) are connected at the distal end of the catheter. (In another embodiment, the device is a dual lumen catheter of side-by-side configuration.) A high osmolality fluid (such as a sterile dextrose solution) flows into the inner lumen to the distal end of the catheter, reverses direction and thus flows back out of the catheter through the outer lumen. The high osmolality fluid is therefore flowing past the inner surface of the semipermeable membrane of the outer catheter wall. In a simple application of this example, the sterile catheter is inserted percutaneously using a sheath or guide wire into a blood vessel, ideally a large vein such as the internal jugular or femoral vein. The use of a sheath has the additional advantage of protecting the potentially fragile outer surface of the catheter during its insertion. The catheter is then anchored in place using skin sutures into a retaining attachment (i.e. plastic wings). The port leading to the inner lumen is then attached to a conventional mechanized pump (not shown), which delivers the sterile hyperosmolar fluid. The fluid flows to the distal tip within the inner lumen and then flows back in the outer lumen to the exit port. In other, less preferred embodiments the device is constructed alternative configurations for supplying fresh hyperosmotic fluid to the inner surface of the semipermeable catheter wall. These include various dual lumen catheters with side-by-side or eccentric channels rather than the preferred coaxial configuration.

In use, it is intended that the device be placed in the lumen of a blood vessel. Veins are preferable to arteries in order to minimize bleeding at the entry site. Although the device can be inserted into the blood vessel, which is under direct observation during an open minor surgical procedure (referred to as a "cut-down"), the preferred and less complicated method is to place it percutaneously. The technique is currently considered a standard practice, and is summarized as follows: Typically, the vein is identified by physical exam or by ultrasonic guidance. The skin covering the vein is prepped by cleaning it with a sterilizing solution. The sterilized field is protected by surrounding it with sterile surgical drapes. Local anesthesia is effected by subcutaneously injecting an anesthetizing medication. A small needle is used to enter the vein, allowing the threading of a guide wire into the vessel. The needle is removed by sliding it off the guide wire, leaving just the wire in place. A flexible, dilating breakaway sheath is slid over the wire and gently pushed into the vein using a twisting motion, thereby using its conical tip to enlarge the hole in the vessel. The guide wire is then removed, leaving the sheath in place. With the stiff wire within the central channel, the ultrafiltration device is slid through the sheath into the blood vessel. The sheath is gently pulled out of the vessel, and discarded by pulling apart its breakaway sides. The ultrafiltration device is then secured to the skin using sutures and, optionally, a wing-like anchor. The stiff wire is then removed. The inlet and outlet tubing ports are then connected to the apparatus supplying and draining the osmotic ultrafiltration fluid. In this configuration, blood remains on the outside of the catheter's semipermeable wall, and the high osmolality fluid traverses its inner surface. Plasma fluid is thereby osmotically driven across the catheter wall into the fluid compartment and exits via the exit port.

Figure 2:
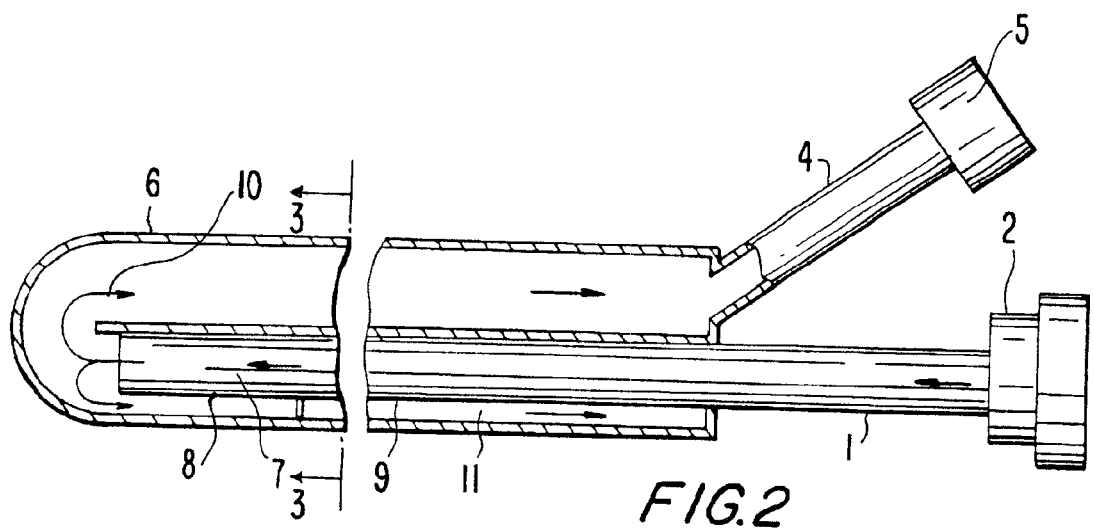
FIG. 2 is a longitudinal cross sectional view of the device.
Figure 3:
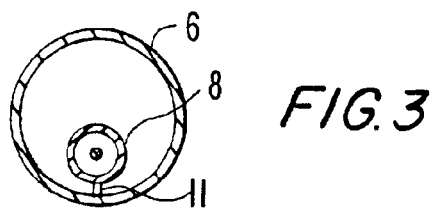
FIG. 3 is a transverse cross-sectional view of the device along line a–a' of FIG. 2.
Figure 4:
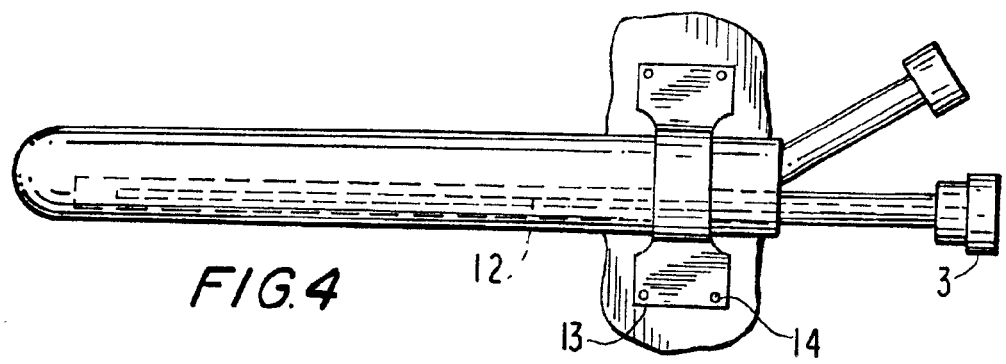
FIG. 4 is a further view of the device of FIG. 2 showing additional elements of the device.

Referring now to the drawings, FIGS. 1–4 illustrate an embodiment of the device wherein the two lumina are coaxially configured. Specifically, FIG. 1 shows in plan view, the catheter of the invention, having outer surface 6 of the main body of the device and which corresponds to the circumferential (outer) lumen of the device, inlet port 1 and outlet port 4, each having attached to the end thereof, luer locking devices 2 and 5 respectively, for connecting inlet port 1 to an external (not shown) source or supply depot for fresh hyperosmotic fluid, and for connecting outlet port 4 to an apparatus (not shown) for draining and collecting used hyperosmotic fluid. Luer lock connector 5 may optionally be fitted with the hub 3 of the stiff wire 12 (described below) used to enhance the stiffness or rigidity of the device during placement thereof. FIG. 2 is a more detailed view in longitudinal cross-section of the device illustrated in FIG. 1. As shown in this drawing figure, central, or inner lumen 7, having wall 8 of nonpermeable polymer is coaxially disposed within the circumferential or outer lumen. Arrows 9 and 10 show the direction of flow of hyperosmotic fluid into and out of the device respectively. More particularly, fluid entering the inlet port 1 flows, as shown by arrow 9 along the length of the inner lumen until it reaches the open, distal end thereof and reverses direction as shown by arrow 10 and ultimately exits the device through outlet port 4 after having removed blood plasma from whole blood during its traverse of the device. FIG. 3, a cross-sectional view along line a–a' of FIG. 2 is provided to illustrate the septum 11 provided between the two lumens to maintain the structural integrity of the device and the integrity of the coaxial geometry of the lumens. FIG. 4 illustrates the stiff wire 12 connected to hub 3 (mentioned above) which may be placed within the central or inner lumen to enhance and maintain the stiffness of the device during its placement in a blood vessel. Additionally as shown in FIG. 4, there is optionally provided an anchor 13 for holding the device securely in place on the surface of a patient's skin while it is in use. Anchor 13, if provided, is provided with holes 14 to enable the anchor to be sutured or otherwise affixed to the patient's skin.

Figure 5:
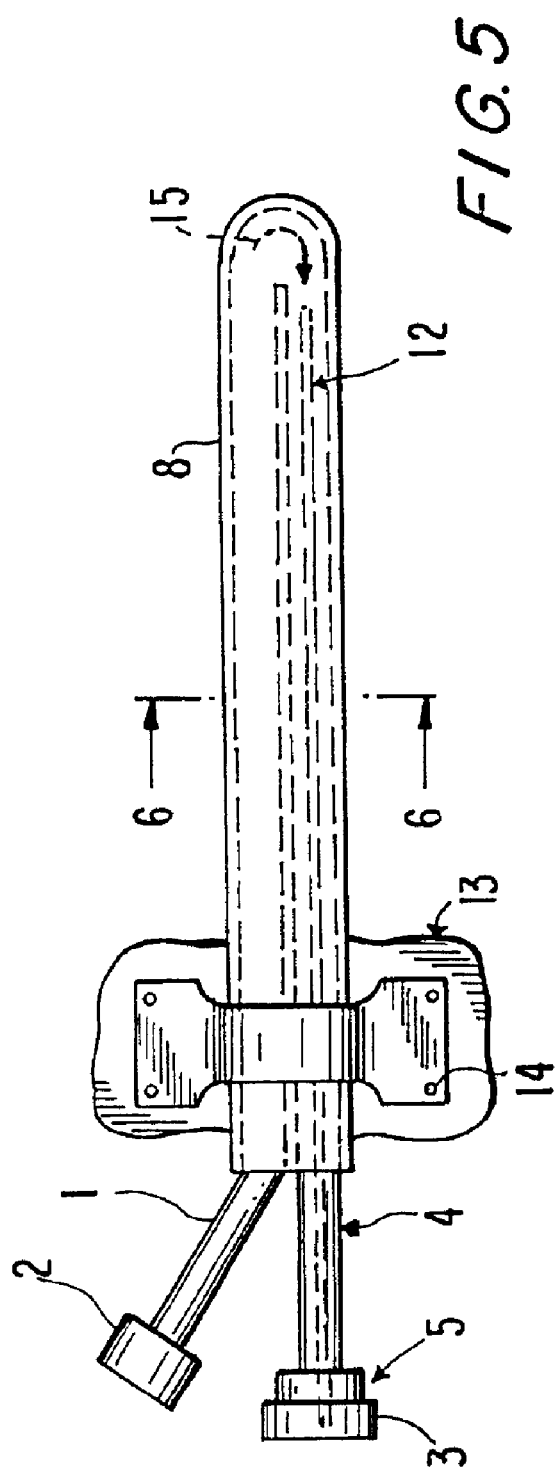
FIG. 5 is an external plan view of a different embodiment of the device.
Figure 6:
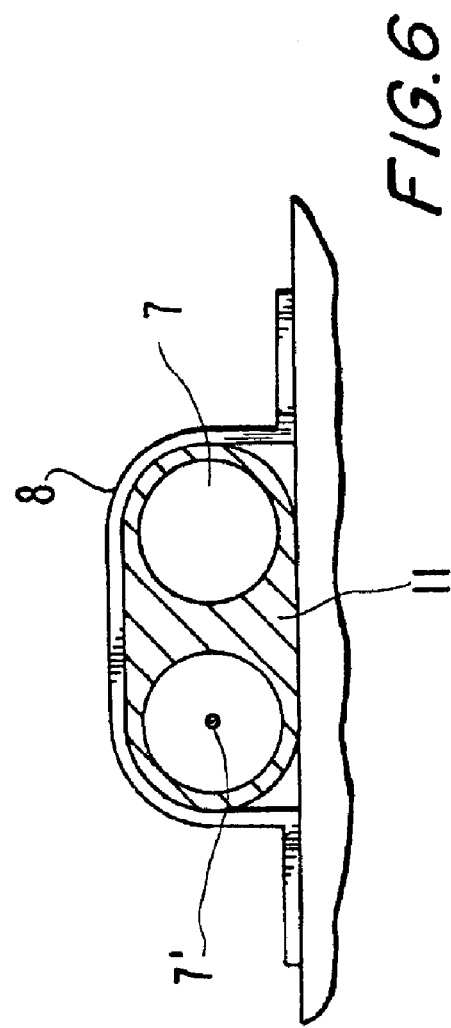
FIG. 6 is a transverse cross-sectional view of the device along the line b–b' of FIG.

FIGS. 5 and 6 illustrate an alternative embodiment of the catheter device wherein the 2 lumens are disposed in a side-by-side configuration, rather than the coaxial configuration shown in FIGS. 1 through 4.

FIG. 5 is an external view of the dual lumen catheter arranged in a side-by-side configuration. Like numbering is used to identify elements common to both configurations. Thus, as seen in FIG. 5, the device is provided with an external surface 8 formed of a semipermeable membrane. The device is provided with inlet port 1 leading to inflow channel 7, corresponding to inner lumen 7, and outlet port 4 connected to outflow channel 11. Luer locks 2 and 5, the latter being optionally provided with hub 3 of stiff wire 12. Wings 13 provided with holes 14 to secure the device to the patient's skin are also provided; and finally, as shown in FIG. 6, which is a transverse cross-sectional view of the embodiment of FIG. 5 illustrates septum 11 provided between the side-by-side lumens to separate them and maintain the structural integrity of the device. Distal end 15 of the catheter is where the inflow 7 and outflow 11 channels or lumens connect.

Coating, caking or clotting on the outside of the catheter is minimized by using a biocompatible material, a small diameter and a pump system which avoids negative hydraulic pressure across and thereby collapsing the wall. The catheter specifications (i.e. length, diameter) and the pump speed are determined by the osmolality of the solution (i.e. 10, 20, or 50% dextrose solutions), the permeability of the outer wall, and are interrelated to achieve the desired ultrafiltration rates.

In a typical application the catheter would be in continuous use and provide slow ultrafiltration for many days. For example, dextrose concentration and pump speed would be set to achieve ultrafiltration of 1–3 ml/min and thereby total about 2–4 liters of fluid removal/day. In embodiments designed for the purpose of effecting highly regulated and controlled fluid removal, the basal pump rate of the hyperosmolar fluid as well as the ultrafiltration rate are achieved using mechanical pumps. In one example, the basal rate of fresh fluid is delivered by a precise inflow pump, and the desired ultrafiltration rate is added to that basal rate to determine the rate of the independent pump on the outflow circuit (i.e. 100 ml/min of 20% dextrose pumped inflow and 102 ml/min pumped outflow to achieve ultrafiltration of 2 ml/min). The parameters of such user-defined pump speeds must be restricted so as to prevent setting an ultrafiltration rate in excess of that produced by the osmotic fluid losses; otherwise there will result a hydraulic convective fluid component to the fluid removal. As indicated above, this vacuum-induced negative hydraulic pressures may cause the catheter to collapse and induce regions of erratically high and low flows across the membrane, thereby causing the system to fail prematurely, as a result of caking of protein or other particulate matter (i.e. fibrin, platelets, or red blood cells).

A number of pumping systems can be used to accomplish this so-called highly regulated fluid removal. As described above, separate inflow and outflow pumps can be utilized. In another embodiment, pumps (i.e. rotating peristaltic or occlusion pumps) or balancing chambers can be utilized to equalize the inflow and outflow rates. Fluid removal can then be accomplished by a separate, highly calibrated pump on the outflow portion of the circuit, placed between the catheter and the equalizing pumps. An alternative pumping system would result in certain advantages such as potential miniaturization, and cost-containment by utilizing a recirculating reservoir of high osmolality solution. For example, if a 10% dextrose solution is otherwise effective, one could instead use a 50% dextrose supplied in an underfilled bag serving as the reservoir for the recirculating luminal fluid. Continuous weighing of the reservoir bag would enable one to monitor the fluid removal and serve as a fail safe mechanism in addition to setting the pump rates as mentioned above. In still another embodiment, there could be a single pump from the reservoir into the catheter's inner lumen and the rate of that pump would be regulated by a feedback mechanism based on the rate of fluid accumulating in the weighed reservoir. Since these reservoir embodiments would be self-contained systems lasting many hours, they would also have advantages from a cost and nursing labor point of view. Overall, and regardless of the exact pumping configuration, the device and pumps would have a very high safety profile because of the long history of successful design and use of dual lumen catheters, and because the flow paths are connected to sealed sterile systems. In the event that a leak occurs, it would still be extremely safe because of the use of sterile solutions, i.e. sugar solutions. Safety can be further improved by placing a blood leak detector on the outflow track (e.g. tubing placed on an external optical sensor set to the proper wavelength to detect the presence of hemoglobin). Catheter longevity can be optimized by the choice of the biocompatible material, such as a synthetic polymer or silicone derivative. Longevity may be further enhanced by intermittently providing positive internal pressure and causing momentary hydraulic outflow from the lumen across the wall and into the blood vessel. The transient reversal of the flow direction would serve to debride or clean the catheter surface. This could be accomplished by many mechanical means, including momentary restriction of the outflow track or altering the relative pump speeds.

Notably, the composition of the semipermeable catheter membrane is selected depending on the sieving characteristics desired to produce the ultrafiltrate. For example, in the simplest embodiment designed to treat congestive heart failure (fluid overload), the wall characteristics are those which are calculated to remove just plasma water with limited removal of small sized electrolytes (such as sodium, potassium, chloride, bicarbonate or small toxins) but lacking pores large enough to remove plasma proteins (i.e. albumin, immunoglobulins). In still another embodiment, the pores can be selected to be much larger and thereby allow removal of larger substances, such as proteins, similar to plasmapheresis. However, as indicated above the flow rates would typically be so low as to limit the total daily mass clearance of these larger moieties.

What is claimed is:

1. An intravascular device for removing plasma fluid from a patient's blood, said device comprising (a) a dual lumen intravascular catheter having open and closed ends wherein the lumina are coaxially disposed as a central core channel and a circumferential outer channel within said catheter, said channel containing the inner lumen, said inner lumen having near and distal ends and being open at both the near end and distal end of the device; (b) inlet and outlet tubing ports at the near open end of the inner lumen and the open end of the outer lumen respectively, said inlet port communicating with the inner lumen configured to allow a fresh hyperosmotic fluid to pass into the inner lumen and out through the distal open end of the core channel and then flow back through the circumferential outer lumen and out of the device through the outlet tubing port, which communicates with the outer lumen; (c) the outer lumen being defined by the circumferential channel of the coaxial configuration and formed between the core channel and the inner surface of the outer catheter wall comprising a semipermeable membrane and having its outer surface so positioned to directly contact whole blood passing by it; (d) said inner lumen being formed from a nonpermeable polymer, so arranged as to permit a continuous supply of fresh hyperosmotic fluid to the outer lumen and thereby exert sufficient osmotic pressure to force plasma fluid from the blood, crossing from the outer to inner surfaces of the circumferential semipermeable wall, into said outer lumen and thence out the outflow port, said device further comprising luer locks disposed at each of the ends of the inlet and outlet ports, and wherein the luer lock disposed at the end of the outlet port further comprises a guide wire having a hub at one end thereof, said hub being removably secured to said luer lock.

2. A device according to claim 1, wherein the semipermeable membrane is a polymeric flexible membrane selected from the group consisting of hydrophilic polyamides, hydophilically modified fluorocarbons, polyether sulfones, siloxanes, polysiloxanes and polysulfones.

3. A device according to claim 2, wherein the semipermeable membrane is a hydrophilic polyamide having a high ultrafiltration coefficient and a molecular weight cut-off below that of the hyperosmotic fluid.

4. A device according to claim 3, wherein the hyperosmotic fluid is a dextrose solution and the molecular weight cut-off is below about 180 Daltons.

5. A device according to claim 1, wherein the nonpermeable membrane is a polyurethane, a derivative of silicone or silastic.

6. A device according to claim 5, wherein the nonpermeable membrane is a polyurethane.

7. A device according to claim 1 and further comprising a septum for separating the two lumens and maintaining structural rigidity of the catheter.

8. A device according to claim 1 and further comprising an anchor provided with a plurality of holes, said anchor being adapted to be circumferentially arranged about the device for securing the device to a tissue surface of a patient using said holes while the device is in use.

9. A device according to claim 1 and further comprising inflow and outflow pumps attached respectively to the inlet and outlet ports for regulating and controlling the flow of hyperosmotic fluid into and out of the device, and thereby also regulating the rate of plasma fluid removal from the patient's blood.

10. A device as claimed in claim 1, wherein the semipermeable membrane is porous to enable plasma removal, the size of the pores being selected depending upon whether it is desired to remove only plasma and small electrolytes or plasma and larger substances including proteins.

11. A method for removing plasma fluid from a patient in need thereof, said method comprising inserting the device as claimed in claim 1 into a selected blood vessel of a patient and introducing a hyperosmolar fluid which is an aqueous solution of a material selected from the group consisting of dextrose, disaccharides, oligosaccharides, starches and low molecular weight dextrans into the inlet port of the device, causing plasma to be driven through the outer wall of the catheter by the osmotic pressure exerted by the hyperosmolar fluid and into said fluid which then flows out of the outlet port of the device.

12. A method as claimed in claim 11, wherein the blood vessel is a vein.

13. A method as claimed in claim 12, wherein the vein is a major vein.

14. A method as claimed in claim 13, wherein the vein is the internal jugular or femoral vein.

15. A method as claimed in claim 11, wherein the material is dextrose.

16. A method as claimed in claim 15, wherein the concentration of the dextrose solution is about 10 to 50% by weight.

17. A method as claimed in claim 11, wherein the pressure exerted by the hyperosmolar fluid flowing through the outer lumen causes distention of said outer lumen, thereby aiding in keeping the pores open.

18. A method as claimed in claim 11 and further comprising periodically reversing the flow of the hyperosmolar fluid using hydraulically driven means to debride the outer surface of the catheter and increase its longevity and performance characteristics.

19. An intravascular device for removing plasma fluid from a patient's blood, said device comprising (a) a dual lumen intravascular catheter having an outer wall, said outer wall being semipermeable and further having open and closed ends wherein the lumina are disposed in a side-by-side configuration with an inflow channel and an outflow channel within said catheter said inflow and outflow channels being separated by a nonpermeable septum, said inflow channel having open ends at both the near end and distal ends of the device; (b) inlet and outlet tubing ports at the near open end of the inflow channel and the open end of the outflow channel respectively, said inlet port communicating with the inflow channel for enabling a fresh hyperosmotic fluid to pass into the inflow channel and out through the distal open end of the inflow channel and then flow back through the outflow channel and out of the device through the outlet tubing port, which communicates with the outflow channel; (c) the outflow channel being defined and formed by a surface on the outer catheter wall comprising to directly contact whole blood passing by it; (d) said inflow channel being formed from a nonpermeable polymer, so arranged as to permit a continuous supply of fresh hyperosmotic fluid to the outflow channel and thereby exert sufficient osmotic pressure to force plasma fluid from the blood, crossing from the outflow channel into said outflow channel and thence out the outflow port; said device further comprising luer locks disposed at each of the ends of the inlet and outlet ports, and wherein the luer lock disposed at the end of the outlet port further comprises a guide wire having a hub at one end thereof, said hub being removably secured to said luer lock, said device further comprising luer locks disposed at each of the ends of the outlet ports, and wherein the luer lock disposed at the end of the outlet port further comprises a guide wire having a hub at one end thereof, said hub being removably secured to said luer lock.

20. A device according to claim 19, wherein the semipermeable membrane is a polymeric flexible membrane selected from the group consisting of hydrophilic polyamides, hydophilically modified fluorocarbons, polyether sulfones, siloxanes, polysiloxanes and polysulfones.

21. A device according to claim 20, wherein the semipermeable membrane is a hydrophilic polyamide having a high ultrafiltration coefficient and a molecular weight cut-off below that of the hyperosmotic fluid.

22. A device according to claim 21, wherein the hyperosmotic fluid is a dextrose solution and the molecular weight cut-off is below about 180 Daltons.

23. A device according to claim 19, wherein the nonpermeable membrane is a polyurethane, a derivative of silicone or silastic.

24. A device according to claim 23, wherein the nonpermeable membrane is a polyurethane.

25. A device according to claim 19 and further comprising a septum for separating the two channels and maintaining structural rigidity of the catheter.

26. A device according to claim 19 and further comprising an anchor provided with a plurality of holes, said anchor being adapted to be circumferentially arranged about the device for securing the device to a tissue surface of a patient using said holes while the device is in use.

27. A device according to claim 19 and further comprising inflow and outflow pumps attached respectively to the inlet and outlet ports for regulating and controlling the flow of hyperosmotic fluid into and out of the device, and thereby also regulating the rate of plasma fluid removal from the patient's blood.

28. A device as claimed in claim 19, wherein the semipermeable membrane is porous to enable plasma removal, the size of the pores being selected depending upon whether it is desired to remove only plasma and small electrolytes or plasma and larger substances including proteins.

* * * * *